United States Patent [19]

Braithwaite et al.

[11] Patent Number: 5,627,303

[45] Date of Patent: May 6, 1997

[54] PREPARATION OF ISOPHORONE

[75] Inventors: John Braithwaite, Charleston; Manuk Colakyan, South Charleston, both of W. Va.

[73] Assignee: Union Carbide Chemicals & Plastics Technology Corporation, Danbury, Conn.

[21] Appl. No.: 405,921

[22] Filed: Mar. 16, 1995

Related U.S. Application Data

[63] Continuation of Ser. No. 112,092, Aug. 25, 1993, abandoned.

[51] Int. Cl.[6] .................................................. C07C 45/45
[52] U.S. Cl. .................................................. 568/388
[58] Field of Search ............................. 568/388, 353

[56] References Cited

U.S. PATENT DOCUMENTS

| | | | |
|---|---|---|---|
| 2,601,624 | 6/1952 | Owen et al. | 252/463 |
| 2,627,506 | 2/1953 | Hunter et al. | 252/463 |
| 4,053,568 | 10/1977 | Hermann et al. | 423/419 P |
| 4,086,188 | 4/1978 | Reichle | 252/463 |
| 4,165,339 | 8/1979 | Reichle | 260/586 |
| 4,170,609 | 10/1979 | Turner | 260/586 C |
| 4,458,026 | 7/1984 | Reichle | 502/80 |
| 4,471,070 | 9/1984 | Siefert et al. | 502/302 |
| 4,472,532 | 9/1984 | Mooi | 502/302 |
| 4,476,324 | 10/1984 | Reichle | 568/388 |
| 4,492,677 | 1/1985 | Yoo et al. | 423/244 |
| 4,535,187 | 8/1985 | Papa et al. | 568/353 |
| 4,656,156 | 4/1987 | Misra | 502/415 |
| 4,970,191 | 11/1990 | Schutz | 502/341 |
| 5,055,620 | 10/1991 | Schutz | 568/353 |
| 5,087,781 | 2/1992 | Schutz et al. | 585/409 |
| 5,104,987 | 4/1992 | King | 544/401 |
| 5,142,077 | 8/1992 | Martin et al. | 554/76 |
| 5,144,089 | 9/1992 | Arena et al. | 568/463 |
| 5,153,156 | 10/1992 | Schutz | 502/63 |
| 5,202,496 | 4/1993 | Schutz et al. | 568/388 |
| 5,214,142 | 5/1993 | King | 544/111 |
| 5,237,107 | 8/1993 | Ishino et al. | 568/463 |
| 5,240,692 | 8/1993 | Morifuji et al. | 432/431 |
| 5,258,558 | 11/1993 | Arena et al. | 568/881 |

FOREIGN PATENT DOCUMENTS

| | | | |
|---|---|---|---|
| 0095783 | 12/1983 | European Pat. Off. | 568/388 |
| 0476785 | 3/1992 | European Pat. Off. | 568/388 |
| 0512843 | 11/1992 | European Pat. Off. | 568/388 |
| 0539002 | 4/1993 | European Pat. Off. | 568/388 |
| 0597693 | 5/1994 | European Pat. Off. | 568/388 |
| WO9012645 | 1/1990 | WIPO | 568/388 |

OTHER PUBLICATIONS

*Clay Minerals*, vol. 19, pp. 591–603, (Article) by R.M. Taylor (1984).

*The United States Pharmacopeia*, pp. 52–53 and 790–791, Twenty–Second Revision, (USP XXII; NF XVII), 1990.

*Applied Catalysis*, vol. 54 (1989) pp. 79–90; "Stabilized Magnesia: A Novel Catalyst (Support) Material" by H. Schaper, et al.

*Catalysis Today*, vol. II, No. 2, pp. 172–299; "Hydrotalcite--Type Anionic Clays: Preparation, Properties And Applications" By F. Cavani, et al. (1991).

*Primary Examiner*—James H. Reamer
*Attorney, Agent, or Firm*—N. L. Balmer

[57] ABSTRACT

This invention relates to the selective preparation of isophorone via aldol condensation of acetone using a calcined magnesium/aluminum mixed oxide catalyst derived from water-insoluble aluminum hydroxide carbonate hydrate and a water-insoluble magnesium carbonate compound.

17 Claims, No Drawings

PREPARATION OF ISOPHORONE

This application is a continuation of prior U.S. application Ser. No. 08/112,092 , filing date Aug. 25, 1993 , now abandoned.

BACKGROUND OF THE INVENTION

1. Field of the Invention

This invention relates to the preparation of isophorone (3,5,5-trimethyl-2-cyclohexen-1-one) and mesityl oxide (4-methyl-3-penten-2-one) via aldol condensation of acetone. More particularly this invention relates to the use of a calcined magnesium/aluminum mixed oxide catalyst for the aforesaid process in order to selectively produce isophorone.

2. Background Art

Gas phase aldol condensation of acetone is well known and a number of methods have been disclosed for converting acetone into a wide variety of products, particularly isophorone and mesityl oxide, which are used in industrial solvents and as chemical intermediates for resins, dyes, and the like. In addition numerous by-products and low value high boilers and tars are also produced. Thus there is a strong desire in the art to control the condensation of the acetone to produce mainly isophorone and mesityl oxide, minimize the formation of by-products, and to control the molar ratio of these two products and various types of catalysts have been proposed to purportedly achieve such results.

For instance U.S. Pat. No. 4,970,171 advances the use of a polymorphic magnesium-aluminum oxide composition as a catalyst for aldol condensation of acetone to isophorone, said catalyst having been prepared by mixing a pseudoboehimite and acid solution to form a gel which is then reacted with magnesium oxide (or hydroxide) to form a mixed metal (e.g. magnesium and aluminum) hydroxide which is subsequently dried and calcined. U.S. Pat. No. 5,153,156 is directed to spray drying a slurry of a synthetic clay of magnesium-aluminum hydroxide, then plasticizing, drying and calcining the mixture into a desired aldol condensation catalyst for producing isophorone. U.S. Pat. No. 4,458,026 discloses the use of a catalyst which is described as a "MgAl—$CO_3$ Hydrotalcite Catalyst", prepared by precipitation using water soluble salts such as $Mg(NO_3)_2 \cdot 6H_2O$ and $Al_2(NO_3)_3 \cdot 9H_2O$ together with sodium carbonate, for the production of isophorone. U.S. Pat. No. 5,144,089 promotes the production of 2-ethyl-2-hexenal by aldol condensation using a solid solution of magnesium oxide-aluminum oxide as the catalyst. The use of various other mixed metal oxide catalysts for isophorone preparation via aldol condensation of acetone are discussed in U.S. Pat. No. 4,535,187 which promotes the use of a catalyst prepared by introducing an inorganic or organic calcium salt onto an alumina support. In contrast the present invention employs a catalyst composition containing magnesium and aluminum that is different from those described in said art and which is made by a different and far simpler catalyst production procedure.

DISCLOSURE OF THE INVENTION

It is an object of this invention to provide an aldolization process for efficiently producing isophorone and mesityl oxide and more preferably selectively isophorone, from acetone using a calcined magnesium/aluminum mixed oxide catalyst derived from an aqueous mixture of a water-insoluble aluminum hydroxide carbonate hydrate compound and a water-insoluble magnesium carbonate compound. Other objects and advantages of this invention will become readily apparent from the following written description and appended claims.

Accordingly, a generic aspect of this invention can be described as a vapor phase aldolization process for producing isophorone and mesityl oxide from acetone which comprises contacting said acetone with a calcined magnesium/aluminum mixed oxide catalyst derived from an aqueous mixture consisting of from about 0.1 to about 5 parts by weight of a water-insoluble magnesium carbonate selected from the group consisting of magnesium carbonate hydroxide pentahydrate, anhydrous magnesium carbonate, magnesium carbonate monohydrate, and magnesium carbonate hydroxide trihydrate, per one part by weight of a water-insoluble aluminum hydroxide carbonate hydrate, and from about 1 to about 10 parts by weight of water per one part of the total weight of said water-insoluble aluminum and magnesium compounds employed.

Of course it is to be understood that, if desired, the water-insoluble magnesium carbonate employed herein could consist of a mixture of any two or more of said recited magnesium carbonate compounds, although it is generally preferred to employ only one magnesium carbonate compound at a time. Moreover as used herein in the catalyst definition of this invention, the term "oxide" embraces oxides, hydroxides, and/or mixtures thereof.

DETAILED DESCRIPTION

As noted above, this invention resides in the employment of a calcined magnesium/aluminum mixed oxide catalyst that is different from catalysts heretofore employed for the production of isophorone and mesityl oxide from acetone. Moreover, such catalysts are considered to be novel compounds and are the subject of assignee's concurrently filed U.S. patent application, Ser. No. 112,583, entitled "Magnesium/Aluminum Mixed Oxide Catalysts", the entire application of which is encompassed herein by reference thereto.

Said calcined magnesium/aluminum mixed oxide catalysts employable in this invention are derived from an aqueous mixture consisting of from about 0.1 to about 5 parts by weight, preferably from about 0.5 to about 5 parts by weight of the water-insoluble magnesium carbonate per one part by weight of the water-insoluble aluminum hydroxide carbonate hydrate, and from about 1 to about 10 parts by weight, preferably from about 1 to about 5 parts by weight of water per one part of the total weight of said water-insoluble aluminum and magnesium compounds employed. More preferably said aqueous mixtures consist of from about 1 to about 3 parts by weight of the water-insoluble magnesium carbonate per one part by weight of the water-insoluble aluminum hydroxide carbonate hydrate, along with from about 1 to about 3 parts by weight of water per one part of the total weight of said water-insoluble aluminum and magnesium compounds employed. Moreover said aqueous mixtures are preferably employed in the form of a smooth paste made by simply thoroughly mixing the two solid water-insoluble magnesium and aluminum salts with water under ambient conditions such as at about room temperature and in any suitable manner desired. Of course, it is to be understood that while said aqueous mixtures (or paste) must contain a minimum amount of about 1 part by weight of water per one part of the total weight of said water-insoluble aluminum and magnesium compounds employed, the upper limit on the amount of water present is not critical and need only be governed by obvious practical constraints and common sense. Any excess or undesirable amounts of water present may be readily filtered out of the aqueous mixture or paste prior to employing it as taught here. It is to be further understood that the aqueous mixture starting material or paste can be the result of mixing dry water-insoluble aluminum and magnesium salts with water or by combining aqueous or wet slurries of said salts along with additional added water if necessary. Preferably distilled or deionized water is employed, although such may not be absolutely necessary.

The water-insoluble aluminum hydroxide carbonate hydrate compounds employable herein may be obtained from Aldrich Chemical Co., Inc. under the designation aluminum hydroxide hydrate, powder or from Chattem Chemicals under such designations as aluminum hydroxide gel and aluminum hydroxide gel, dried. Such materials comprise an amorphous hydrated form of aluminum hydroxide in which there is a partial substitution of carbonate for hydroxide as explained e.g. on page 52 of The United States Pharmacopeia, Twenty-Second Revision, (USP XXII; NF XVII), 1990.

Illustrative water-insoluble magnesium carbonate compounds that may be employable herein, along with companies that supply same, include magnesium carbonate hydroxide pentahydrate (Aldrich Chemical Co., Inc.), anhydrous magnesium carbonate (Eastman Fine Chemicals), magnesium carbonate monohydrate (J. T. Baker Inc.) and magnesium carbonate hydroxide trihydrate (Pfaltz and Bauer Inc.). The preferred magnesium carbonate compound is magnesium carbonate hydroxide pentahydrate.

Accordingly a unique feature of said catalysts, and one that is considered critical to the excellent performance of the calcined magnesium/aluminum mixed oxide catalysts for selectively producing isophorone, over prolonged periods of time, is the presence of carbonate in both the magnesium and aluminum starting materials. The absence of such carbonate in either starting material has been found to result in catalysts that do not provide as good an isophorone product selectivity over comparable catalytic activity life spans as the catalysts of this invention.

If desired, calcined magnesium/aluminum mixed oxide catalyst powders of this invention may be readily obtained by directly calcining the above-described aqueous mixtures or pastes of said water-insoluble magnesium and aluminum salts at any suitable temperature, e.g. from about 250° C. to about 800° C. and preferably from about 300° C. to about 500° C., for a sufficient period of time to produce the desired catalyst, in any conventional known manner. In general periods of time ranging from about 2 to about 24 hours should be sufficient to complete most calcinations. Moreover the calcination (or heat) treatment may be carried out in any suitable furnace or oven e.g. a muffle furnace, or in air or an inert gas stream or even under vacuum. Of course it is to be understood that too low or too high a calcination temperature should be avoided for obvious conventional reasons and that optimum calcination temperatures may be readily determined by routine experimentation. In general it may be preferred to employ calcination temperatures which maximize the catalyst surface area and pore volume of the amorphous like calcined magnesium/aluminum mixed oxide product. The calcined magnesium/aluminum mixed oxide catalyst powders so obtained may be employed directly in their powdered form, e.g. in the case of batch-type base catalyzed processes. More preferably such catalysts may be tableted or extruded in any conventional manner desired to form particles which are wear and impact resistant and can function more effectively in commercial continuous fixed bed type catalyzed processes.

More preferably the calcined magnesium/aluminum mixed oxide catalysts employable in this invention are obtained by (a) hydrothermally treating the above-described aqueous mixtures or pastes of said water-insoluble magnesium and aluminum salts at a temperature of from about 80° C. to about 250° C. for a sufficient period of time to obtain a hydrotalcite type mixed magnesium/aluminum hydroxide carbonate catalyst precursor, (b) formulating said catalyst precursor into shaped particles, and (c) drying and calcining the particulate shaped catalyst precursor.

This particular preferred procedure for obtaining calcined magnesium/aluminum mixed oxide catalysts affords one with a far simpler method for producing a hydrotalcite type mixed metal hydroxide carbonate precursor, than presently advocated in the prior art, while at the same time providing a far simpler method for directly obtaining the ultimately more desired particulate shaped calcined magnesium/aluminum mixed oxide catalysts. Moreover it is submitted that the simplicity of this particular preferred procedure of the subject invention facilitates replication of any particular desired calcined magnesium/aluminum mixed oxide catalyst.

The hydrothermal treatment of the above defined aqueous mixtures or pastes of said water-insoluble magnesium and aluminum salts of this invention is carded out for a sufficient period of time in order to convert the aqueous pastes into a hydrotalcite type mixed magnesium/aluminum hydroxide carbonate catalyst precursor, which may be evidenced by the initiation of metal oxygen metal bond formation, as seen by the diminishing X-ray diffraction pattern of the discrete magnesium carbonate salt employed and the beginning of at least the partial appearance of a hydrotalcite type X-ray diffraction pattern within the hydrothermal treated paste. While the hydrothermal treatment may be carried out in any suitable manner, it is recommended and preferred to carry out said treatment in an open environment so as to freely and simultaneously evolve both water and carbon dioxide from the aqueous starting material (e.g. paste) in order to obtain the more preferred calcined catalysts, i.e., those which may provide the best degree of desired isophorone product selectivity and longest catalyst life. Thus it is recommended to avoid hydrothermal treatment conditions that do not simultaneously evolve both water and carbon dioxide (e.g. use of a water condenser during said treatment) as well as hydrothermal treatments in which the temperatures employed are not sufficient enough to simultaneously evolve both water and carbon dioxide from the aqueous paste starting material (e.g. merely air drying). Accordingly, the preferred hydrothermal treatment temperatures employable herein may range from about 100° C. to about 175° C. and more preferably from about 110° C. to about 150° C.

Moreover, while the hydrotalcite type catalyst precursors could be directly calcined in the same manner as described above for directly calcining the aqueous paste starting materials of this invention, such a procedure would again result in a calcined catalyst in powder form, and as noted above it is more preferred to obtain and/or employ the calcined catalyst as a shaped particulate in continuous catalyzed process operations that require a particulate fixed catalyst bed in order to be commercially attractive.

It is to be understood that while the hydrothermal treatment conditions necessary in order to achieve the most desired optimum results may depend, to a large extent on the experience of the operator of said procedure, such preferred hydrothermal treatment conditions may be readily ascertainable by following the teachings of this invention and routine experimentation. For example one preferred hydrothermal heat treatment involves the passing of the above described aqueous paste starting materials of this invention through a steam heated thermal screw at about 150° C. until hydrotalcite type, readily extrudable catalyst precursors are obtained.

The hydrotalcite type catalyst precursors can be readily formulated into any desired particulate shaped materials, such as tablets (including pills, pellets, etc.), extrudates, and the like. For instance said catalyst precursors can be formulated into conventional extrusions, e.g. ⅛" or 1/16" extrusions, via any conventional extruder. Alternatively, said precursors can be formulated into conventional tablets, e.g. ⅛" by ⅛" tablets, via any conventional molding technique, such as by mixing the catalyst precursor with a small amount, e.g. 0.5 to 2 weight percent of a suitable mold releasing lubricant, e.g graphite, and the like, and punching out the desired tablets. The mold releasing lubricant is of course removed (burned off) from the catalyst during calcination. In general it is preferred to employ the calcined catalysts herein in their tableted form.

Finally, the formulated particulate shaped hydrotalcite type catalyst precursors are dried and calcined in any conventional known manner, such as already described herein and as disclosed e.g. in U.S. Pat. No. 5,214,142.

The intermediate drying step of the particulate shaped material just prior to calcination is merely a conventional mild heating procedure that is commonly carried out in the art to gradually preheat the moist particulate shaped materials prior to subjecting them to the higher temperatures of calcination, in order to help prevent the non-calcined particulate materials from experiencing too severe a thermal shock, i.e., rupturing or disintegration of the particulate shaped materials due to too rapid a water and/or gas loss caused by the high calcination temperatures. Accordingly, any suitable predrying procedure may be employed herein such as by placing the particulate shaped non-calcined materials in a drying oven and drying them for several hours, e.g. from 2 to 24 hours, at temperatures of about 80° C. to about 250° C. More preferably such temperatures may range from about 100° C. to about 200° C., while a drying temperature of about 150° C. for 2 to 12 hours should be suitable for most purposes.

The calcination of said dried particulate shaped materials may be carried out in any conventional manner desired, such as already discussed herein above. As previously noted calcination temperatures of from about 250° C. to about 800° C. may be employed, while preferred calcination temperatures preferably range from about 300° C. to about 500° C. Again the calcination (or final heat) treatment may be carried out in any conventional furnace or oven such as a muffle furnace, or in air, or an inert gas or even under vacuum and in any conventional known manner desired.

While calcination of hydrotalcite type mixed metal hydroxides catalyst precursors is known to produce mixed metal oxide catalysts of an amorphous nature, it is to be understood that the calcined magnesium/aluminum mixed oxide catalysts employable in this invention are believed to also still contain some hydroxide and/or carbonate anions in view of their presence in the water-insoluble salts of the aqueous paste starting materials and/or hydrotalcite type mixed metal complex catalyst precursors of this invention.

The vapor or gas phase aldolization of acetone to isophorone and mesityl oxide of this invention may be carried out in any conventional known manner such as disclosed, e.g. in U.S. Pat. Nos. 4,458,026 and 4,535,187. In general the process of this invention is carried out by passing acetone vapor over a fixed bed of the solid catalyst. The catalysts of this invention do not require a support or binder and can be employed into any desired form, e.g. as powers, granules, tablets, spheres, extrudates, and the like. Preferably the catalysts are employed in the form of extrudates or tablets. More preferably it is recommended to employ the catalysts herein in their tableted form, rather than in their extruded form, since such tablets appear to have a better and more consistently reproducible crush strength than their comparative extruded counterparts. Moreover, while such is not necessary, if desired the catalysts can also be formulated to be carried on an inert material. Most preferably the catalysts employed herein are free from any support material and/or binder.

The preferred temperature for converting acetone to isophorone and mesityl oxide using the catalysts of this invention is about 250° C. to about 350° C., with a temperatures ranging from about 260° C. to about 320° C. being more preferred. Pressure is not narrowly critical. If desired the conversion of acetone with the catalysts of this invention can be effected at atmospheric and below, as well as higher atmospheric pressures. Thus the reaction may be carried out at a pressure in the range of from about 1 to about 200 atmospheres, while preferred pressures are atmospheric or slightly above, such as from about 1 to about 10 atmospheres.

Preferred acetone feeds that may be employed include acetone having a purity of at least about 80, and more preferably at least about 90 percent by weight acetone with the balance being water (which is an inert). Of course it is to be understood that said balance may also possibly contain minor impurities such as mesityl oxide, and other materials such as isopropanol, isopropyl ether and the like, although such are generally not desired in the acetone feed. An anhydrous acetone feed having a purity of about 98 percent by weight or greater with the balance being water is an especially useful feed for gathering comparative data. The feed rate of acetone is not narrowly critical. In general efficient results may be achieved with an acetone feed rate in the range of about 20 to about 140 pounds of acetone per hour per cubic foot of catalyst. Alternatively, hourly vapor space velocities of about 90 to about 700 cubic feet of gaseous acetone per cubic foot of catalyst per hour may be employed. The preferred contact time is generally only a matter of a few seconds, e.g. about 5 to about 40 seconds. Moreover it is generally preferred to operate the process under such conditions that the percent conversion of acetone is held within the range of about 7 to about 40 percent by weight, and more preferably from about 10 to about 35 percent by weight. Too low a conversion of acetone makes the process commercially unattractive, while too high a conversion may cause too excessive a product yield loss due to undesirable side reactions.

The desired isophorone and mesityl oxide products along with unreacted acetone and conventional by-products of the process may be recovered and analyzed in any conventional manner and with equipment and techniques well known to those skilled in the art.

Thus while the catalysts employable in this invention are highly efficient for producing both isophorone and mesityl oxide, they are especially selective towards the production of isophorone over that of mesityl oxide. Such selectivity which allows for the production of a higher percentage of isophorone to be produced per pound of converted acetone can be very desirable commercially. Moreover, the catalysts employable in this invention have also been found to be highly effective even at very high acetone feed rates, e.g.

when liquid acetone is passed through a preheater vaporization zone of a tubular reactor at a rate of about two volumes of feed per volume of catalyst per hour. Thus, more isophorone can be produced in a given amount of time using the same reactor, or alternatively a smaller reactor can be employed to produce a comparative amount of isophorone. The catalysts employable in this invention have also been found to be effective over long periods of continuous operation, i.e. they have a long catalyst life.

The following examples are illustrative of the present invention and are not to be regarded as limitative. It is to be understood that all parts, percentages and proportions referred to herein and in the appended claims are by weight unless otherwise indicated.

Catalyst Preparation

A series of calcined magnesium-aluminum mixed oxide catalysts were prepared by mixing various molar amounts of a water-insoluble aluminum hydroxide carbonate hydrate and magnesium carbonate hydroxide pentahydrate with water to form a paste. Both water and carbon dioxide were then removed from the paste to produce a mixed magnesium-aluminum carbonate catalyst precursor which was then either extruded into extradates or mixed with a mold release lubricant, and punched out in tablet form, and then dried and calcined.

The various molar amounts of water-insoluble carbonate compounds employed as well as the characterization of the prepared calcined catalysts are given in Examples 1–6 and Table I below. The catalyst crush strengths were determined by ASTM test D4179.

EXAMPLE 1

A total of 1000 grams of magnesium carbonate hydroxide pentahydrate from Aldrich Chemical Co., Inc., and 1000 grams of aluminum hydroxide carbonate hydrate (aluminum hydroxide hydrate, powder from Aldrich Chemical Co., Inc.) along with 5000 grams of deionized water were mixed together to form a slurry in an Eirich mixer. The slurry was then hydrothermally treated in a thermal screw at 150° C. and the resulting paste was formed into ⅛ inch extrudates in an extruder. The extrudates were dried at 150° C. in an oven, and then placed in a calcination oven and calcined at 400° C. for 6 hours to give a calcined magnesium/aluminum mixed oxide catalyst having a Mg/Al oxide molar ratio of about 1.9:1. The catalyst is referred to hereinafter as Catalyst A.

EXAMPLE 2

A total of 996 grams of magnesium carbonate hydroxide pentahydrate and 1663 grams of aluminum hydroxide carbonate hydrate (aluminum hydroxide gel, dried from Chattam Chemicals) along with 7977 grams of deionized water were mixed together to form a slurry in an Eirich mixer. The slurry was then hydrothermally treated in a thermal screw at 150° C. and the resulting paste was formed into ⅛ inch extrudates in an extruder. The extrudates were dried at 150° C. in an oven, and then placed in a calcination oven and calcined at 300° C. for 4 hours to give a calcined magnesium/aluminum mixed oxide catalyst having a Mg/Al oxide molar ratio of about 1.1:1. The catalyst is referred to hereinafter as Catalyst B.

EXAMPLE 3

A total of 2000 grams of magnesium carbonate hydroxide pentahydrate and 824 grams of aluminum hydroxide carbonate hydrate (aluminum hydroxide gel, dried from Chattam Chemicals) along with 5648 grams of deionized water were mixed together to form a slurry in an Eirich mixer. The slurry was then hydrothermally treated in a thermal screw at 128° C. and the resulting paste was formed into ⅛ inch extrudates in an extruder. The extrudates were dried at 150° C. in an oven, and then placed in a calcination oven and calcined at 425° C. for 4 hours to give a calcined magnesium/aluminum mixed oxide catalyst having a Mg/Al oxide molar ratio of about 4.4:1. The catalyst is referred to hereinafter as Catalyst C.

EXAMPLE 4

A total of 1792 grams of magnesium carbonate hydroxide pentahydrate and 975 grams of aluminum hydroxide carbonate hydrate (aluminum hydroxide gel, dried from Chattam Chemicals) along with 8341 grams of deionized water were mixed together to form a slurry in an Eirich mixer. The slurry was then hydrothermally treated in a thermal screw at 107° C. and the resulting paste was formed into ⅛ inch extrudates in an extruder. The extrudates were dried at 150° C. in an oven, and then placed in a calcination oven and calcined at 300° C. for 4 hours to give a calcined magnesium/aluminum mixed oxide catalyst having a Mg/Al oxide molar ratio of about 3.3:1. The catalyst is referred to hereinafter as Catalyst D.

EXAMPLE 5

A total of 996 grams of magnesium carbonate hydroxide pentahydrate and 1663 grams of aluminum hydroxide carbonate hydrate (aluminum hydroxide gel, dried from Chattam Chemicals) along with 7977 grams of deionized water were mixed together to form a slurry in an Eirich mixer. The slurry was then hydrothermally treated in a thermal screw at 150° C. and the resulting paste was mixed with about 2 weight % graphite and punched into ⅛ inch by ⅛ inch tablets. The tablets were dried at 150° C. in an oven, and then placed in a calcination oven and calcined at 450° C. for 4 hours to give a calcined magnesium/aluminum mixed oxide catalyst having a Mg/Al oxide molar ratio of about 1.1:1. The catalyst is referred to hereinafter as Catalyst E.

EXAMPLE 6

A mixture having a 1.65 mole ratio of $MgO:Al_2O_3$ was prepared by mixing magnesium carbonate hydroxide pentahydrate and aluminum hydroxide carbonate hydrate (aluminum hydroxide gel, dried from Chattam Chemicals) along with a 2:1 weight ratio of deionized water to powder to form a slurry in an Eirich mixer. The slurry was then hydrothermally treated in a thermal screw at 150° C. until a sample of the resulting paste showed about a 70 percent weight loss on ignition at 1000° C. The resulting paste was then mixed with about 2 weight % graphite and punched into ⅛ inch by ⅛ inch tablets. The tablets were dried at 150° C. in an oven, and then placed in a calcination oven and calcined at 307° C. for 4 hours to give a calcined magnesium/aluminum mixed oxide catalyst have a Mg/Al oxide molar ratio of about 1.65:1. The catalyst is referred to hereinafter as Catalyst F.

EXAMPLES 7 to 14

Aldolization

The catalysts so prepared in Examples 1–6 were then employed to produce isophorone and mesityl oxide via the aldol condensation of various acetone feeds using the reaction conditions reported in Table I below, which also reports the results of such experiments in terms of the production of isophorone and mesityl oxide. The by-products consisted essentially of miscellaneous high boilers, e.g. tetralones and xylitone.

In said Table I the following calculations were employed.

$$\text{Conversion (\%)} = \frac{\text{Equivalents of Acetone Consumed}}{\text{Equivalents of acetone Fed}} \times 100$$

$$\text{Efficiency (\%)} = \frac{\text{Equivalents of Acetone in the Isophor-one and Mesityl Oxide Recovered}}{\text{Equivalents of Acetone Consumed}} \times 100$$

Moreover the recorded amounts of isophorone and mesityl oxide reported in said Table I include the minor amounts (e.g. less than 1.0 wt. %) of their respective isomers, i.e. 3,5,5-trimethyl-3cyclohexen-1-one and 4-methyl-4-penten-2-one, that are also produced.

passed in a downward direction over the catalyst. The sandbath temperature was regulated by a temperature controller, and the reaction pressure was controlled with appropriate valves. Following the reactor the reaction products were condensed against a propylene glycol cooled heat exchanger. A sample valve was installed after the condenser and samples collected into a dry ice bath. Any off-gas was measured by a dry gas meter.

The reactor samples were analyzed by gas chromatography and normalized for water content using Karl Fischer water titration.

TABLE I

| | Catalyst | | | | | | | |
| --- | --- | --- | --- | --- | --- | --- | --- | --- |
| Examples | 7 | 8 | 9 | 10 | 11 | 12 | 13 | 14 |
| Catalyst Used | A | A | B | B | C | D | E | F |
| Catalyst Shape | Extrudate | Extrudate | Extrudate | Extrudate | Extrudate | Extrudate | Tablet | Tablet |
| MgO/Al$_2$O$_3$ (molar ratio) | 1.9:1 | 1.9:1 | 1.1:1 | 1.1:1 | 4.4:1 | 3.3:1 | 1.1:1 | 1.65:1 |
| Vol. of Catalyst (cc) | 200 | 200 | 200 | 200 | 200 | 200 | 200 | 200 |
| Space Velocity (lbs of feed acetone/ft$^3$ of cat./hr) | 66.6 | 99.9 | 96.7 | 98 | 97.7 | 101.6 | 51.1 | 97.7 |
| Space Velocity in vol. of equiv. liquid acetone feed/vol. of cat./hr. (hr$^{-1}$) | 1.35 | 2 | 1.96 | 2 | 1.98 | 2.06 | 1.03 | 1.98 |
| Acetone Feed (wt %) | 99.87 | 94.19 | 99.96 | 99.96 | 99.97 | 99.59 | 99.5 | 98.44 |
| Water in Feed (wt %) | 0.13 | 5.81 | 0.04 | 0.04 | 0.03 | 0.41 | 0.5 | 1.56 |
| Temp. °C. | 280 | 280 | 270 | 290 | 280 | 290 | 270 | 260 |
| Pressure (psig) | 13 | 20 | 40 | 40 | 40 | 40 | 40 | 40 |
| Hours on Stream | 91 | 307 | 89 | 137 | 113 | 213 | 458 | 281 |
| Isophorone wt % | 13.29 | 9.48 | 10.64 | 16.4 | 10.49 | 9.68 | 12.4 | 9.83 |
| Mesityl Oxide wt % | 3.39 | 3.01 | 3.64 | 3.09 | 4.43 | 3.22 | 4.06 | 4.05 |
| *MSO/IØ (mol/mol) | 0.36 | 0.45 | 0.48 | 0.27 | 0.59 | 0.46 | 0.46 | 0.58 |
| Conversion wt % | 25.92 | 19.24 | 20.97 | 31.34 | 21.96 | 19.31 | 24.4 | 20.39 |
| Efficiency (mol %) | 80.23 | 85.62 | 84.55 | 77.67 | 84.14 | 83.28 | 84.04 | 85.63 |
| +Cat. Surface Area (m$^2$/g) | 199 | 199 | 355 | 355 | 154 | 73 | 126 | 136 |
| ++Cat. Pore Vol. (cc/g) | — | — | 1.11 | 1.11 | 1.4 | 1.09 | 0.65 | 0.64 |
| Cat. Bulk Density (lbs/ft$^3$) | — | — | 21.5 | 21.5 | 19.7 | 20.4 | 34.9 | 35.6 |
| Cat. Crush Strength (lbs) | — | — | 7.3 | 7.3 | 9.9 | 10.9 | 8.2 | 11.8 |

*MSO/IØ = Mesityl Oxide/Isophorone
+BET N$_2$ Adsorption
++Hg Porosimetry

The aldol condensations of said Table I were all carried out employing a one-inch pilot plant reactor as described below.

Pilot Plant Reactor

This device consisted of a 1"×3' tube made of 304 stainless steel which is immersed into an electrically heated air fluidized sandbath. The central part of the tube contained approximately 200 cc of catalyst. At the tube outlet (base) was placed a stainless steel mesh (size #16), and on either end of the catalyst bed were packed a zone of 6 mm diameter glass beads. Three thermocouples, spaced at equal intervals throughout the catalyst bed, were available to monitor the bed temperature and were located into the center of the tube through 1/16" thermocouple wells. Liquid acetone was pumped with a reciprocating pump into a preheater located in the sandbath. The preheater consisted of a ¾"×12" steel tube packed with 6 mm diameter glass beads. Acetone vapor was then introduced into the top of the reactor tube and The mole ratio of mesityl oxide to isophorone product given in the Examples of Table I above is shown to be less than 1.0 which demonstrates the high selectivity of the process of this invention for producing isophorone as compared to mesityl oxide. Note also the high molar efficiencies for producing both isophorone and mesityl oxide of Examples 7 to 14.

Various modifications and variations of this invention will be obvious to a worker skilled in the art and it is to be understood that such modifications and variations are to be included within the purview of this application and the spirit and scope of the appended claims.

What is claimed is:

1. A vapor phase aldolization process for producing isophorone and mesityl oxide from acetone which comprises contacting said acetone with a calcined magnesium/aluminum mixed oxide catalyst derived from an aqueous mixture consisting of from about 0.1 to about 5 parts by weight of a water-insoluble magnesium carbonate selected from the group consisting of magnesium carbonate hydroxide pentahydrate, anhydrous magnesium carbonate, magnesium carbonate monohydrate, and magnesium carbonate hydroxide trihydrate, per one part by weight of a water-insoluble aluminum hydroxide carbonate hydrate, said catalyst being calcined at a temperature of from about 300° C. to about 500° C. and from about 1 to about 10 parts by weight of water per one part of the total weight of said water-insoluble aluminum and magnesium compounds employed, and recovering an aldolization product of isophorone, mesityl oxide and unreacted acetone.

2. A process as defined in claim 1, wherein the vapor phase aldolization process is carried out at a temperature of about 250° C. to about 350° C.

3. A process as defined in claim 2, wherein said process is carried out at a temperature of about 260° C. to about 320° C.

4. A process as defined in claim 2, wherein said process is carried out at a pressure of about 1 to 200 atmospheres.

5. A process as defined in claim 3, wherein said process is carried out at a pressure of about 1 to about 10 atmospheres.

6. A process as defined in claim 2, wherein the water-insoluble magnesium carbonate compound is magnesium carbonate hydroxide pentahydrate.

7. A process as defined in claim 2, wherein the water-insoluble magnesium carbonate compound is anhydrous magnesium carbonate.

8. A process as defined in claim 2, wherein the water-insoluble magnesium carbonate compound is magnesium carbonate monohydrate.

9. A process as defined in claim 2, wherein the water-insoluble magnesium carbonate compound is magnesium carbonate hydroxide trihydrate.

10. A process as defined in claim 4, wherein the water-insoluble magnesium carbonate compound is magnesium carbonate hydroxide pentahydrate.

11. A process as defined in claim 10, wherein the catalyst is employed in its extruded form.

12. A process as defined in claim 10, wherein the catalyst is employed in its tableted form.

13. A process as defined in claim 1, wherein the aqueous mixture consists of from about 0.5 to about 5 parts by weight of the water-insoluble magnesium carbonate per one part by weight of the water-insoluble aluminum hydroxide carbonate hydrate, and from about 1 to about 5 parts by weight of water per one part of the total weight of said water-insoluble aluminum and magnesium compounds employed.

14. A process as defined in claim 10 wherein the aqueous mixture consists of from about 1 to about 3 parts by weight of the water-insoluble magnesium carbonate per one part by weight of the water-insoluble aluminum hydroxide carbonate hydrate, and from about 1 to about 3 parts by weight of water per one part of the total weight of said water-insoluble aluminum and magnesium compounds employed.

15. A process as defined in claim 13, wherein the catalyst was obtained by (a) hydrothermally treating the aqueous mixture of said water-insoluble magnesium and aluminum salts at a temperature of from about 80° C. to about 250° C. for a sufficient period of time to obtain a hydrotalcite type mixed magnesium/aluminum hydroxide carbonate catalyst precursor, (b) formulating said catalyst precursor into shaped particles, and (c) drying and calcining the particulate shaped catalyst precursor.

16. A process as defined in claim 3, wherein the catalyst was obtained by (a) hydrothermally treating the aqueous mixture of said water-insoluble magnesium and aluminum salts at a temperature of from about 80° C. to about 250° C. for a sufficient period of time to obtain a hydrotalcite type mixed magnesium/aluminum hydroxide carbonate catalyst precursor, (b) formulating said catalyst precursor into shaped particles, and (c) drying and calcining the particulate shaped catalyst precursor.

17. A process as defined in claim 16, wherein the catalyst is employed in its tableted form.

* * * * *